United States Patent [19]
Baldeschwieler et al.

[11] Patent Number: 4,931,361
[45] Date of Patent: * Jun. 5, 1990

[54] CRYOPROTECTIVE REAGENTS IN FREEZE-DRYING MEMBRANES

[75] Inventors: John D. Baldeschwieler; Raymond P. Goodrich, Jr., both of Pasadena, Calif.

[73] Assignee: California Institute of Technology, Pasadena, Calif.

[*] Notice: The portion of the term of this patent subsequent to Apr. 10, 2007 has been disclaimed.

[21] Appl. No.: 273,952

[22] Filed: Nov. 18, 1988

[51] Int. Cl.$^5$ ............... B01J 13/02; A61K 37/22; A61K 35/14

[52] U.S. Cl. ............... 428/402.2; 264/4.1; 424/533; 424/450; 436/829; 514/971; 435/2

[58] Field of Search ............... 428/402.2; 424/450, 424/101, 94.3; 436/829; 264/4.1, 4.3; 514/971; 34/5

[56] References Cited

U.S. PATENT DOCUMENTS

| | | | |
|---|---|---|---|
| 4,004,975 | 1/1977 | Lionetti et al. | 424/101 X |
| 4,229,360 | 10/1980 | Schneider et al. | 428/402.2 X |
| 4,247,411 | 1/1981 | Vanlerberghe et al. | 428/402.2 X |
| 4,310,505 | 1/1982 | Baldeschwieler et al. | 428/402.2 X |
| 4,476,221 | 10/1984 | Kane et al. | 424/101 X |
| 4,766,046 | 8/1988 | Abra et al. | 424/450 |
| 4,772,471 | 9/1988 | Vanlerberghe et al. | 424/450 |
| 4,806,343 | 2/1989 | Carpenter et al. | 424/450 |

OTHER PUBLICATIONS

*Intern. J. Pharm,* vol. 33, G. J. Fransen et al., "Critical Parameters in Freezing of Liposomes", (1986), pp. 27–35.

*Primary Examiner*—Matthew A. Thexton
*Assistant Examiner*—John M. Covert
*Attorney, Agent, or Firm*—Ashen Golant Martin & Seldon

[57] ABSTRACT

The ability of phosphoglyceride-containing membranes to withstand the disruptive effects of freezing, thawing, or freeze-drying is enhanced when treated with (a) a compound of the formula $R-X-R_1$, wherein R is a lipid or lipophilic anchor, X is a hydrophilic linker group, and $R_1$ is a polyalcohol or carbohydrate group, and (b) ascorbic acid.

14 Claims, No Drawings

CRYOPROTECTIVE REAGENTS IN FREEZE-DRYING MEMBRANES

ORIGIN OF INVENTION

This invention was made with support from the U.S. Government through the U.S. Army Research Office under Grant number DAAL-03-87-K-0044 and also with support from the National Institute of General Medical Sciences under National Research Service Award T32GM07616. The U.S. Government has certain rights in the invention.

RELATED APPLICATION

The present invention is an improvement over the invention disclosed and claimed in our copending application Ser. No. 07/128,152, filed Dec. 3, 1987.

TECHNICAL FIELD

This invention relates to cryoprotection and preservation of lipid membrane structure through freezing, freeze-drying, and thawing, and in particular to stabilization of phosphoglyceride vesicle structures under such conditions.

BACKGROUND ART

In our copending application Ser. No. 07/128,152, filed Dec. 3, 1987, and entitled "Cryoprotective Reagent", we have noted that carbohydrates have demonstrated the capacity to stabilize membrane structures under the severe conditions of dehydrations and freezing. These membranes are composed of ampiphilic lipid molecules in a bilayer arrangement. When the lipids associate with each other in such a configuration, they form a barrier with polar regions oriented toward the aqueous layers and a hydrophobic interior. This barrier constitutes the main structural arrangement of cell membranes and liposomal structures, which are often employed as model membrane systems or drug delivery systems.

In the absence of carbohydrates, membranes which are subjected to freeze drying, undergo fusion and intermixing of membrane lipids. In addition, the membranes lose their natural barrier properties and leak materials entrapped in the inner aqueous layer to the surrounding media. The use of carbohydrates added to the external aqueous media as well as the inner hydrophilic region, prevents these phenomena from occurring. Thus, membranes of cells or liposomes treated with carbohydrates maintain structural stability.

The amounts of carbohydrates employed to provide protection is on an equimolar level with the amount of membrane phospholipid present in the membranes. This imposes several limitations. Addition of the carbohydrate to the external media alone does not afford adequate protection. The levels of carbohydrate employed makes sample handling difficult and inefficient and impose potentially deleterious osmotic effects on the membrane.

Copending application Ser. No. 07/128,152 discloses and claims improved cryoprotectants comprised of a lipophilic molecule (such as a sterol), a molecule having polyhydroxyl groups (such as a carbohydrate), and a hydrophilic unit (such as polyoxyethylene) linking the lipophilic molecule with the molecule having polyhydroxy groups. These compositions elicit significantly more pronounced effects than free carbohydrates due to the attachment of the carbohydrate to the membrane directly. This alleviates problems associated with osmotic stress on the membrane and the difficulties encountered with the use of large amounts of material. The use of these agents also alleviates the problems associated with the placement of the carbohydrate on both the inner and outer faces of the membrane.

Crowe et al in "Factors affecting the stability of dry liposomes" [sic], Biochimica et Biophysica Acta 939 (1988), pp. 327–334, reported that a small amount of negatively charged lipid in the bilayer significantly increases stability. However, the negative charge in such compositions is membrane-bound and has adverse effects on circulation lifetimes of the liposomes.

DISCLOSURE OF INVENTION

The ability of phosphoglyceride-containing membranes, whether biological or synthetic, to withstand the disruptive effects of freezing, thawing, or freeze-drying, is enhanced when treated with a composition disclosed and claimed in our copending application Ser. No. 07/128,152, filed Dec. 3, 1987, to which ascorbic acid has been added. Ascorbic acid alone has no effect on the preservation of membrane structural integrity following freeze drying. This is evidenced by leakage of vescile contents and loss of membrane constituents via intermembrane fusion.

This invention is useful in a range of medical and laboratory applications. It greatly enhances the capabilities for storage of synthetic or biological materials (such as liposomes containing nutrients, hemoglobin or any fluid, red blood cells, or any membrane-bound component) in an anhydrous and/or frozen state while preserving their functional integrity.

In general, the advantages of this invention can be obtained by applying to a phosphoglyceride-containing membrane (a) from about 10 to about 40 mole% of a compound of the formula

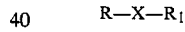

$$R-X-R_1$$

wherein R is a lipid or a lipophilic anchor which is suitable for intercalation into a phosphoglyceride bilayer, X is a hydrophilic linker group, and $R_1$ is a polyalcohol or carbohydrate group, and (b) ascorbic acid.

BEST MODES FOR CARRYING OUT THE INVENTION

The ascorbic acid is advantageously added to suspensions of lipid and an $R-X-R_1$ compound. Preferred amounts are in the range between about 40 mM and 100 mM. Improved stability is noticeable with as little as 0.05 mole of the $R-X-R_1$ compound per mole of lipid, but is most pronounced at the ratio of 0.4 mole carbohydrate per mole of lipid. Higher levels of carbohydrate do not significantly improve the degree of protection.

As noted in our co-pending application, the anchor R can be a lipid or a steroid and the $R_1$ compound can be a polyalcohol or a carbohydrate. For instance, $R_1$ can be cholesterol or other steroids, as well as fatty acids and phospholipid derivatives.

The X portion of the above formula can be a hydrophilic linker, such as polyoxyethylene, preferably containing at least two oxyethylene groups. Polyalcohols such as inositol or carbohydrates, such as galactose or glucose, preferably disaccharides such as maltose, trehalose, or sucrose or dextran, are used to form the terminal group $R_1$.

The following derivatives of cholesterol are prepared in accordance with the procedures set forth in our copending application Ser. No. 07/128,152 and the references cited therein:

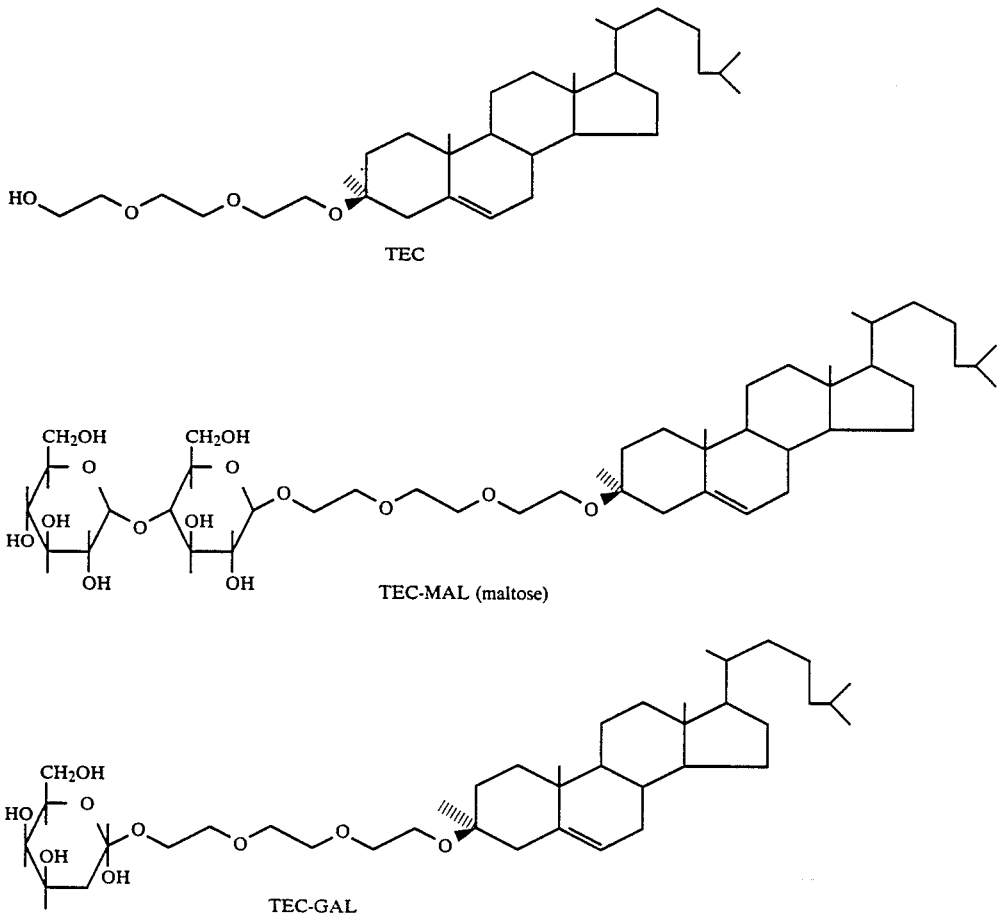

INDUSTRIAL APPLICABILITY

This invention is useful in a range of medical and laboratory applications. It greatly enhances current capabilities for storage of synthetic or biological materials (such as vesicles containing nutrients or any fluid, red blood cells, or any membrane-bound component) in an anhydrous and/or frozen state while preserving their functional integrity.

EXAMPLE 1

Aqueous suspensions of vesicles were prepared by bath sonication of 6.4 μmoles 1-palmitoyl-2-oleoyl-sn-glycero--phosphatidylcholine (POPC) in 500 μl buffered solutions containing 10 mM TES, 120 mM sodium chloride, 0.1 mM EDTA and 50 mM L-(+)-ascorbic acid at pH 7.0 with varying molar proportions of TEC-Mal. For the Resonance Energy Transfer (RET) assay, samples contained 1 mole% fluorescent probes based on the total lipid content. A donor probe of N-(7-nitro-2,1-benzoxadiazol-4-yl) dipalmitoyl phosphatidylethanolamine was used in one vesicle population. An acceptor probe of N-(lissamine rhodamin B sulfonyl) dioleoyl phosphatidylethanolamine was used in the acceptor vesicles. Energy transfer between donor and acceptor vesicles depends on distance of separation of probe molecules. High levels of transfer indicate close proximity and thus fusion of donor and acceptor vesicles.

For carboxyfluorescin retention experiments, 12.8 mM egg phosphatidylcholine (Egg PC) and varying molar proportions of TEC-Mal were bath sonicated in a triethylene sulfonic acid (TES) buffer containing 10 mM TES, 120 mM sodium chloride, 0.1 mM EDTA, 50 mM L-(+)-ascorbic acid and 100 mM carboxyfluorescein at pH 7.0. The carboxyfluorescein self-quenches at high concentrations such as those that occur in the interior aqueous compartment of vesicles. When released, the fluorescence intensity is increased. By monitoring fluorescence intensity in freeze dried vesicles, it is possible to access leakage of vesicle contents.

An aliquot of 200 microliters (100 μL donor and 100 μL acceptor) of vesicles was frozen in liquid nitrogen and placed on the lyophilizer for 16 to 18 hours. The samples were rehydrated with 200 microliters of distilled water. The results are recorded in Table I.

TABLE I

| Mixing and Retention Data | | |
|---|---|---|
| Ratio of TEC-Mal/lipid | % Probe Mixing | % CF Retention |
| 0.0 | 95 | 5 |
| 0.05 | 40 | 43 |
| 0.11 | 21 | 70 |
| 0.25 | 19 | 100 |
| 0.43 | 5 | 100 |

The results show that vesicles undergo minimum lipid mixing (i.e., fusion) and maximum retention of contents in the presence of 0.25-0.43 mole TEC-Mal/Lipid.

EXAMPLE 2

The experiments described in Example 1 were repeated using various additives in place of TEC-Mal. All other details are as described in Example 1.

TABLE II

| Additive | Moles/Mole Lipid | % Probe Mixing | % CF Retention |
|---|---|---|---|
| Cholesterol | 0.0 | 90 | 5 |
| | 0.05 | 87 | 0 |
| | 0.11 | 91 | 7 |
| | 0.25 | 83 | 11 |
| | 0.43 | 94 | 3 |
| TEC | 0.0 | 90 | 5 |
| | 0.05 | — | 0 |
| | 0.11 | 95 | 19 |
| | 0.25 | 97 | 3 |
| | 0.43 | 97 | 19 |
| TEC-Gal | 0.0 | 90 | 5 |
| | 0.05 | — | 22 |
| | 0.11 | 63 | 24 |
| | 0.25 | 54 | 27 |
| | 0.43 | 41 | 38 |

These results show that only TEC-Gal demonstrates moderate levels of protections with respect to membrane fusion and leakage. No other compound is as effective as TEC-Mal, however.

EXAMPLE 3

Vesicles of POPC at a concentration of 12.8 mM with 0.43 mole Additive/mole lipid were prepared by bath sonication in TES buffer at pH 7.0 containing 10 mM TES, 120 mM sodium chloride, and 0.1 mM EDTA. One sample set was prepared with buffer containing 50 mM L-(+)-ascorbic acid and one sample set was prepared without. Vesicles were frozen in liquid nitrogen and lyophilized for 16 to 18 hours. Samples were rehydrated with distilled water. Vesicle sizes were measured before and after freeze drying using dynamic light scattering at an angle of 90°. Vesicle fusion results in the formation of larger vesicles. Hence, damage to membranes via fusion may be monitored by assessing increases in vesicle size following freeze-drying.

TABLE III

| SAMPLE | +ASCORBIC ACID | −ASCORBIC ACID |
|---|---|---|
| POPC | | |
| Before | 49.2 +/− 13.2 nm | 48.8 +/− 11.8 nm |
| After | 736.6 +/− 661.2 nm | 1430 +/− 473 nm |
| POPC:CHOL | | |
| Before | 51.6 +/− 13.6 nm | 53.9 +/− 16.4 nm |
| After | 598.2 +/− 439.1 nm | 2170 +/− 396 nm |
| POPC:TEC | | |
| Before | 29.2 +/− 7.0 nm | 27.8 +/− 6.0 nm |
| After | 2260 +/− 312 nm | 2080 +/− 387 nm |
| POPC:TEC-Gal | | |
| Before | 32.7 +/− 7.7 nm | 33.8 +/− 7.8 nm |
| After | 954 +/− 677.2 nm | 1930 +/− 391 nm |
| POPC:TEC-Mal | | |
| Before | 55.0 +/− 23.3 nm | 61.3 +/− 19.3 nm |
| After | 52.4 +/− 25.9 nm | 2140 +/− 392 nm |

As the results indicate, ascorbic acid is necessary to maintain vesicle size and integrity. This is most pronounced for samples containing TEC-Mal.

EXAMPLE 4

Two sets of Egg PC vesicles at a concentration of 12.8 mM were prepared with varying proportions of TEC-Mal by bath sonication of lipids in a 10 mM TES, 120 mM sodium chloride, 0.1 mM EDTA, and 100 mM carboxyfluorescein buffer at pH 7.0. One set of vesicles was prepared in buffer which also contained 50 mM L-(+)-ascorbic acid. This placed ascorbic acid on both the inner and outer surfaces of the vesicle. The second set of vesicles was prepared in the same buffer without the ascorbic acid. To this set was added after sonication sufficient ascorbic acid to raise the concentration to 50 mM. Since ascorbic acid does not penetrate membranes easily, it can be localized in this case only on the outer surface of the membranes.

Aliquots of 200 microliters were frozen in liquid nitrogen and placed on a lyophilizer for 16 to 18 hours. Samples were reconstituted with 200 microliters of distilled water.

TABLE IV

| | Outer vs Outer-Inner Ascorbic Acid | |
|---|---|---|
| Mole Ratio | % CF Retention | |
| TEC-Mal/Lipid | Outer | Outer + Inner |
| 0.0 | 0 | 5 |
| 0.05 | 53 | 43 |
| 0.11 | 75 | 70 |
| 0.25 | 92 | 100 |
| 0.43 | 100 | 100 |

As shown in Table IV, ascorbic acid on the outside only is sufficient to provide adequate protection for the membrane.

EXAMPLE 5

Egg PC:TEC-Mal (4:1 mole ratio) vesicles at a concentration of 12.8 mM were prepared in TES buffer containing 10 mM TES, 120 mM sodium chloride, 0.1 mM EDTA, and 100 mM carboxyfluorescein at pH 7.0 by bath sonication. Varying amounts of L-(+)-Ascorbic acid was added to vesicles after preparation (e.g., external only). Aliquots of 200 microliters of vesicles were frozen in liquid nitrogen and placed on a lyophilizer for 16 to 18 hours. The samples were rehydrated with distilled water.

TABLE V

| Varying Ascorbic Acid | |
|---|---|
| External Conc. Ascorbic Acid (mM) | % CF Retention |
| 0 | 0 |
| 10 | 30 |
| 20 | 35 |
| 23 | 51 |
| 43 | 85 |
| 60 | 90 |
| 80 | 89 |
| 103 | 100 |

As Table V demonstrates, a minimum of 40 mM external ascorbic acid is required to provide adequate retention of vesicle contents (i.e., >80% retention).

EXAMPLE 6

Vesicles of EGG PC:TEC-Mal (4:1 mole ratio) were prepared as described in Example 5. Samples of amino acids and other compounds were substituted for ascorbic acid. All other experimental details are as described in Example 5. Results are recorded in Table VI.

TABLE VI
Effectiveness of Agents Other Than Ascorbic Acid

| Compound | Concentration | % CF Retention |
|---|---|---|
| L-(+)-Ascorbic Acid | 100 mM | 100 |
| L-Glutamic Acid | 50 mM | 0 |
|  | 100 mM | 0 |
| L-Cysteine | 100 mM | 0 |
| Tris-Hydroxymethyl-aminomethane | 100 mM | 0 |
| Isocitric Acid | 100 mM | 0 |
| L-(+)-Dehydro-ascorbic acid | 100 mM | 0 |

As Table VI demonstrates, only ascorbic acid in the external medium appears to demonstrate a protective action. The effect does not appear to be mediated by charge of the compound or reducing agent capacity.

EXAMPLE 7

Vesicles of Egg PC at a concentration of 12.8 mM were prepared by bath sonication of lipid in a buffer containing 10 mM TES, 120 mM sodium chloride, 0.1 mM EDTA, and 100 mM Carboxyfluorescein at pH 7.0. To this was added an equimolar dispersion of TEC-Mal in TES buffer without the carboxyfluorescein. Samples were incubated at 37° and 47° C. in a water bath for one hour at 22° C. for three hours and subsequently centrifuged at 14,000 rpm for 5 minutes. The supernatants were removed. Sufficient ascorbic acid was added to bring the final concentration in solution to 100 mM. An aliquot of 200 microliters of each of the supernatants was frozen in liquid nitrogen and placed on the lyophilizer for 16 to 18 hours. The vesicles were rehydrated with 200 microliters of distilled water and leakage of carboxyfluorescein was assessed.

TABLE VII
TEC-Mal Incorporation Into Pre-existing Membranes

| Incubation Temperature | % CF Retention |
|---|---|
| 37 | 62 |
| 47 | 92 |
| 22 (3 hrs.) | 83 |

The results in Table VII indicate that addition of TEC-Mal to pre-existing membranes is sufficient to provide protection to these membranes (i.e., TEC-Mal does not need to be added to the vesicle or membrane formulation prior to formation of the membrane structure).

What is claimed is:

1. A composition for the protection of phosphoglyceride-containing biological or synthetic membranes from the disruptive effects of freezing, thawing, or freeze-drying, comprising (a) a compound of the formula $$R-X-R_1$$

wherein R is a lipid or lipophilic anchor which is suitable for intercalation into and incorporation within a phosphoglyceride layer, X is a hydrophilic linker group, and $R_1$ is a polyalcohol or carbohydrate group, and (b) ascorbic acid.

2. The composition of claim 1 wherein said anchor is a lipid.

3. The composition of claim 1 wherein said anchor is a steroid.

4. The composition of claim 1 wherein $R_1$ is a carbohydrate group.

5. The composition of claim 4 wherein $R_1$ is a disaccharide.

6. The composition of claim 1 wherein said ascorbic acid is in the form of sodium ascorbate.

7. A method for the protection of phosphoglyceride-containing biological or synthetic membranes from the disruptive effects of freezing, thawing, or freeze-drying comprising applying to an aqueous solution of said membranes (a) from about 10 to about 40 mole% of a compound of the formula $$R-X-R_1$$

wherein R is a lipid or lipophilic anchor which is suitable for intercalation into and incorporation within a phosphoglyceride layer, X is a hydrophilic linker group, and $R_1$ is a polyalcohol or carbohydrate group, and (b) ascorbic acid.

8. The method of claim 7 wherein the concentration of said sodium ascorbate to said aqueous solution ranges from about 25 to about 500 mM.

9. The method of claim 8 wherein the concentration of said sodium ascorbate to said aqueous solution ranges from about 40 to about 100 mM.

10. The method of claim 7 wherein the anchor is a lipid.

11. The method of claim 7 wherein the anchor is a steroid.

12. The method of claim 7 wherein $R_1$ is a carbohydrate group.

13. the method of claim 12 wherein $R_1$ is a disaccharide.

14. The method of claim 7 wherein said ascorbic acid is in the form of sodium ascorbate.

* * * * *